United States Patent
Larsson

(10) Patent No.: US 8,069,618 B2
(45) Date of Patent: Dec. 6, 2011

(54) STERILIZATION PLANT, EXTENSION MODULE AND METHOD OF INCREASING THE CAPACITY FOR A STERILIZATION PLANT

(75) Inventor: Hol Michael Larsson, Stockholm (SE)

(73) Assignee: Luki AB, Stockholm (SE)

( * ) Notice: Subject to any disclaimer, the term of this patent is extended or adjusted under 35 U.S.C. 154(b) by 646 days.

(21) Appl. No.: 11/815,393

(22) PCT Filed: May 20, 2005

(86) PCT No.: PCT/SE2005/000761
§ 371 (c)(1),
(2), (4) Date: Oct. 17, 2007

(87) PCT Pub. No.: WO2006/078197
PCT Pub. Date: Jul. 27, 2006

(65) Prior Publication Data
US 2008/0098666 A1    May 1, 2008

(30) Foreign Application Priority Data
Feb. 9, 2005 (SE) ..................... 0500318

(51) Int. Cl.
*E04H 1/00* (2006.01)
*E04H 3/00* (2006.01)
*E04H 5/00* (2006.01)
*E04H 6/00* (2006.01)
*E04H 9/00* (2006.01)
*E04H 14/00* (2006.01)
*E04H 6/42* (2006.01)
*E01F 9/00* (2006.01)

(52) U.S. Cl. ............ 52/79.8; 52/79.9; 52/79.12; 52/174
(58) Field of Classification Search ............... 52/79.8, 52/79.9, 79.12, 174
See application file for complete search history.

(56) References Cited

U.S. PATENT DOCUMENTS

| | | | | |
|---|---|---|---|---|
| 4,067,691 | A | * | 1/1978 | McGady et al. ........... 422/1 |
| 5,511,594 | A | * | 4/1996 | Brennan et al. ........... 141/98 |
| 5,727,353 | A | * | 3/1998 | Getz et al. ............... 52/79.1 |
| 5,906,075 | A | * | 5/1999 | Sowers ................... 52/79.8 |
| 7,269,925 | B2 | * | 9/2007 | Lam ....................... 52/79.1 |

FOREIGN PATENT DOCUMENTS

| | | |
|---|---|---|
| DE | 32 29 900 | 2/1984 |
| EP | 0 366 559 | 5/1990 |
| JP | 11-159177 | 6/1996 |

OTHER PUBLICATIONS esp@ce machine translation of EP1930731 (retrieved Apr. 11, 2011).*

* cited by examiner

*Primary Examiner* — Walter Griffin
*Assistant Examiner* — Christopher Vandeusen
(74) *Attorney, Agent, or Firm* — Pearne & Gordon LLP

(57) ABSTRACT

A sterilization plant for the sterilization of surgical instruments is provided. The plant includes at least one original building (1) having at least one first process line that extends, at least partly, essentially parallel to a first one (2) of the essentially limiting external walls (2, 3, 4, 5) of the original building (1). The sterilization plant further includes at least one extension module (31) located next to and, at least partly, essentially parallel to the first external wall (2). Also provided are an extension module (31) and a method of increasing the capacity of a sterilization plant.

13 Claims, 3 Drawing Sheets

STERILIZATION PLANT, EXTENSION MODULE AND METHOD OF INCREASING THE CAPACITY FOR A STERILIZATION PLANT

The present invention relates to a sterilization plant for the sterilization of surgical instruments, the plant comprising at least one original building having at least one first process line, in turn comprising at least one first contaminated zone for the handling of contaminated surgical instruments and at least one first sterile zone for the handling of sterile surgical instruments. The invention also relates to an extension module as well as a method of increasing the capacity of a sterilization plant.

PRIOR ART

U.S. Pat. No. 5,511,594 discloses modular pharmacy system and pharmacy process. The interior spaces may be changed and/or brought to expand as required in order to provide more or less space for an individual workstation or individual room. Additional modular units may be connected. For instance, additional office space may be connected as a modular unit to the left of the modular pharmacy. In the pharmaceutic system, at least one workstation is included for the cleaning or sterilization of equipment from a workstation. The intention here is not to sterilize surgical instruments and the plant does not comprise at least one original building having at least one first process line, in turn comprising at least one first contaminated zone for the handling of contaminated surgical instruments and at least one first sterile zone for the handling of sterile surgical instruments. The publication neither shows any extension module for the use in a sterilization plant nor any method of increasing the capacity of a sterilization plant for the sterilization of surgical instruments.

SUMMARY OF THE INVENTION

A first object of the invention is to provide a sterilization plant for the sterilization of surgical instruments, which sterilization plant is easily extensible. A second object of the invention is to provide an extension module for direct and easy use in a sterilization plant according to the invention. A third object of the invention is to provide an easy way of increasing the capacity of a sterilization plant for the sterilization of surgical instruments.

Thus, the invention comprises a sterilization plant for the sterilization of surgical instruments, the plant comprising at least one original building having at least one first process line, in turn comprising at least one first contaminated zone for the handling of contaminated surgical instruments and at least one first sterile zone for the handling of sterile surgical instruments. Said at least one first process line extends, at least partly, essentially parallel to a first one of the essentially limiting external walls of said original building, the sterilization plant further comprising at least one extension module located next to and, at least partly, essentially parallel to said first external wall and comprising at least one second process line, in turn comprising at least one second contaminated zone for the handling of contaminated surgical instruments and at least one second sterile zone for the handling of sterile surgical instruments.

Said at least one first process line may comprise at least one first clean zone for the handling of clean, but not sterile, surgical instruments and located between said at least one first contaminated zone and said at least one first sterile zone and said at least one second process line may comprise at least one second clean zone for the handling of clean, but not sterile, surgical instruments and located between said at least one second contaminated zone and said at least one second sterile zone.

Said first external wall may have at least one through first passage that connects said at least one first contaminated zone and said at least one second contaminated zone. Said first external wall may have at least one through second passage that connects said at least one first clean zone and said at least one second clean zone. Said first external wall may have at least one through third passage that connects said at least one first sterile zone and said at least one second sterile zone. At least one of said at least one first, second and third passages may consist of at least one emergency exit existing in the original building. Said first external wall may have three emergency exits.

The sterilization plant may comprise at least one storage space intended for transport trolleys or the like, which storage space may be positioned in said original building and extend next to and essentially parallel to said first external wall. Said at least one third passage may run through said storage space for transport trolleys.

Said extension module may have an essentially rectangular shape having three extension external walls, no extension external wall being present along said first external wall. A first one of said extension external walls may have three emergency exits, wherein said first extension external wall may be positioned essentially opposite said first external wall.

Said at least one first process line may comprise at least one entrance for the intake of contaminated instruments in said original building, at least one department for manual rough washing, and at least one instrument dishwasher in said at least one first contaminated zone, at least one packing table and at least one autoclave in said at least one first clean zone as well as at least one exit for the take out of sterile instruments in said at least one first sterile zone.

Thus, the invention also comprises an extension module for the use in a sterilization plant according to the above. The extension module comprises at least one second process line having at least one second contaminated zone for the handling of contaminated surgical instruments and at least one second sterile zone for the handling of sterile surgical instruments.

Said at least one second process line may comprise at least one second clean zone for the handling of clean, but not sterile, surgical instruments and located between said at least one second contaminated zone and said at least one second sterile zone. The extension module may have an essentially rectangular form having three extension external walls. A first one of said extension external walls may have three emergency exits.

Thus, the invention also comprises a method of increasing the capacity of a sterilization plant for the sterilization of surgical instruments, which sterilization plant comprises at least one original building having at least one first process line, in turn comprising at least one first contaminated zone for the handling of contaminated surgical instruments and at least one first sterile zone for the handling of sterile surgical instruments. The method comprises extension of the original building, or of an extension on the original building, by at least one extension module that is placed next to and, at least partly, essentially parallel to a first external wall of the original building, or on the already existing extension, and that comprises at least one second process line having at least one second contaminated zone for the handling of contaminated surgical instruments and at least one second sterile zone for the handling of sterile surgical instruments.

Said at least one first process line may be brought to comprise at least one first clean zone for the handling of clean, but not sterile, surgical instruments and located between said at least one first contaminated zone and said at least one first sterile zone and said at least one second process line may be brought to comprise at least one second clean zone for the handling of clean, but not sterile, surgical instruments and located between said at least one second contaminated zone and said at least one second sterile zone. At least one through first passage may be opened in said first external wall, which passage connects said at least one first contaminated zone and said at least one second contaminated zone. At least one through second passage may be opened in said first external wall, which passage connects said at least one first clean zone and said at least one second clean zone. At least one through third passage may be opened in said first external wall, which passage connects said at least one first sterile zone and said at least one second sterile zone.

LIST OF DRAWINGS

DESCRIPTION OF EMBODIMENTS

Figure 1A:
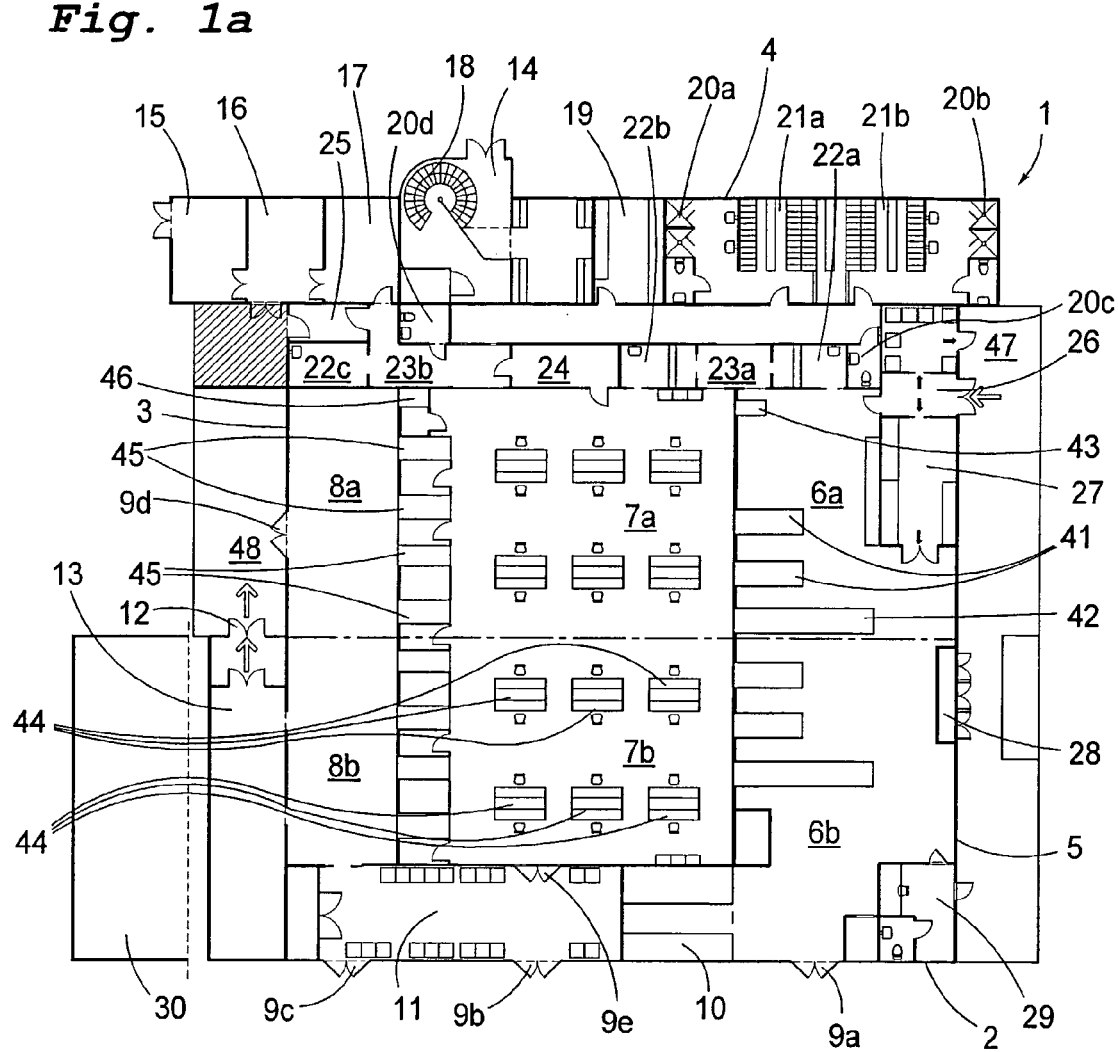
FIG. 1a shows, in a top view, in section and in principle, a lower floor in an original building included in a sterilization plant according to the invention.

In FIG. 1a, it is seen how a lower floor in an original building 1 included in a sterilization plant according to the invention appears. The basic shape of the building 1 is essentially rectangular and is limited by a first external wall 2, a second external wall 3, a third external wall 4, and a fourth external wall 5. In the building 1, two process lines for the sterilization of surgical instruments are present, each process line comprising a contaminated zone 6a, 6b, a clean zone 7a, 7b and a sterile zone 8a, 8b. In addition to these process lines, the following passages and spaces are present in the building 1.

In said first external wall 2, three emergency exits 9a-c are present and inside and along said first external wall 2 a space 10 is present, arranged in said contaminated zone 6b, for the washing of transport trolleys or the like and a storage space 11, arranged in said sterile zone 8b, for transport trolleys or the like. In the space 10, two trolley-washing units are present. In said second external wall 3, an emergency exit 9d and exit 12 are present for the take out of sterilized goods and inside and along said second external wall 3, storage space 13 is present for said sterilized goods, In said third external wall 4, a main entrance 14 is present and inside and along the same external wall 4, a number of service spaces are present, such as room 15 for chemical storage, steam-generator room 16, water-treatment room 17, staircase 18 including elevator and wardrobe, workroom 19 for sterile-service engineer, toilets 20a-d, locker room 21a for women, locker room 21b for men, rooms 22a-c for protective clothing, entries 23a, 23b, storage space 24 for package material or the like, and storage space 25 for raw materials. In said fourth external wall 5, entrance 26 is present for the intake of contaminated goods and inside and along said fourth external wall 5, space 27 is present for manual rough washing, space 28 for vehicle washing equipment as well as driver reception 29 including toilet.

Figure 1B:
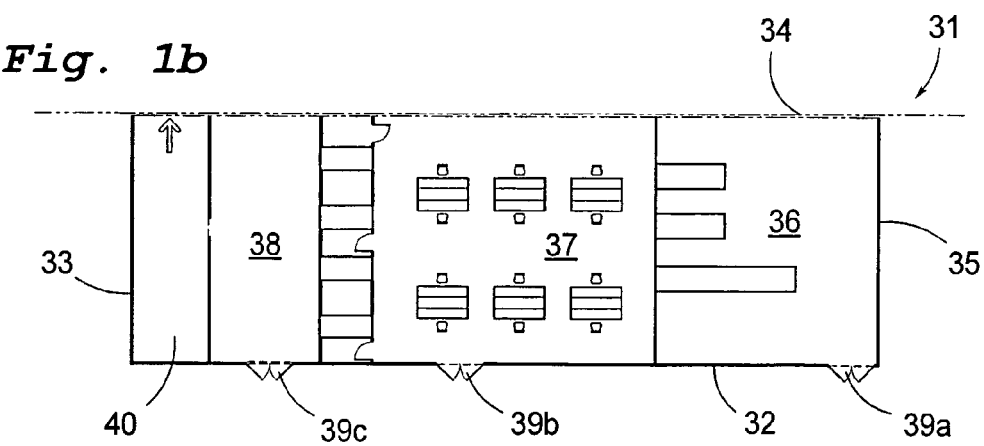
FIG. 1b shows, in a top view, in section and in principle, an extension module according to the invention and included in the sterilization plant according to the invention.

In FIG. 1b it is seen how an extension module 31 according to the invention, and in turn included in a sterilization plant according to the invention, appears. The basic shape of the extension module 31 is essentially rectangular and is limited by a first extension external wall 32, a second extension external wall 33, a third side 34—but no third extension external wall—as well as a fourth extension external wall 35. In the extension module 31, a process line is present for the sterilization of surgical instruments, the process line comprising a contaminated zone 36, a clean zone 37 and a sterile zone 38. In addition to these process lines, following passages and spaces are present in the extension module 31.

In said first external wall 32, three emergency exits 39a-c are present. Inside and along said second external wall 33, a storage space 40 is present for sterilized goods.

Each one of said contaminated zones 6a, 6b, 36, in said original building 1 as well as in said extension module 31, comprises two instrument dishwashers 41 and one multi-chamber dishwasher 42. Furthermore, a fast-processing dishwasher 43 is present in a first contaminated zone 6a of said contaminated zones 6a, 6b,36. Each one of said clean zones 7a, 7b, 37, in said original building 1 as well as in said extension module 31, comprises six double packing tables 44 and four autoclaves 45, i.e., sterilizers 45. Furthermore, a fast-processing autoclave 46 is present in a first clean zone 7a of said clean zones 7a, 7b, 37. In a second sterile zone 8b of said sterile zones 8a, 8b, 38, a storage space 13 is present for sterilized and possibly packed goods. Furthermore, a loading area 47 for contaminated goods adjacent to the entrance 26 and a loading area 48 for sterilized goods adjacent to the exit 12 outside the original building 1 are present. The original building 1 may be provided with additional storage space 30.

Thus, the sterilization plant according to the invention is composed of the original building 1 provided with the extension module 31 according to the invention, the extension module 31 being located next to the original building 1 in such a way that said first external wall 2 in the original building 1 coincides with said third side 34 in the extension module 31. The extension can be easily made since the extension module 31 is open towards said first external wall 2 in the original building 1 and is also, as regards dimensions and design, adapted to the original building 1. The presence of said emergency exits 9a-c in said first external wall 2 also simplifies the connection of the extension module 31 to the original building 1, since it is only necessary to open or remove said emergency exits 9a-c in order to create passages between the respective zones of the same types in the original building 1 and the extension module 31, respectively. However, in order to provide a passage between the clean zones in question, it is required that an additional emergency exit 9e in the storage space 11 is opened or removed and that a partition wall is provided in the storage space 11 in order to separate the clean zones in question from the sterile zones in question. If larger passages are required between the original building 1 and the extension module 31, naturally the entire or parts of said first external wall 2 can be dismantled.

The extension module 31 may be built on-site, next to the original building 1, but may also be completed on another location, complete including floor, three extension external walls, roof and fittings, and be transported to the site of the original building 1 and there be lifted in place by means of a crane or the like. The extension module 31 may then, in turn and in an analogous way, be extended by one or more additional extension modules 31 and the plant may accordingly expand without hindrance, and in view of the need of sterilization of surgical instruments, on the assumption that there is ground space.

Now, the travel of the contaminated goods through the plant will be described briefly. Contaminated surgical instruments, which have been used in operations on hospitals or the like, are received from, for instance, lorry transport, in the loading area 47. The goods are transported by industrial truck, or in another suitable way, through the entrance 26. If the goods are really heavily contaminated, the same may be brought to the space 27 for manual rough washing to be washed there before dishwashing, otherwise the same are normally brought directly to someone of the dishwashers 41-43 in someone of the contaminated zones 6a, 6b, 36. The dishwashing goods are brought, after dishwashing, to someone of the packing tables 44 in someone of the clean zones 7a, 7b, 37, for manual packaging in one or more paper bags and additional envelope material that is semi-permeable. Instead of said paper bags and additional envelope material, the dishwashing goods may be placed in one or more containers including lid, where each lid is provided with a through hole that in turn is covered by a filter. In the clean zones 7a, 7b, 37, overpressure prevails by the action of a ventilating system. The packaged goods are then brought for sterilization to someone of the autoclaves 45 and further out in someone of the sterile zones 8a, 8b, 38 and, via possible intermediate storage in the storage space 13, further out through the exit 12 to the loading area 48 for sterilized goods. From here, the goods may be collected for transportation to users of the surgical equipment.

Figure 2A:
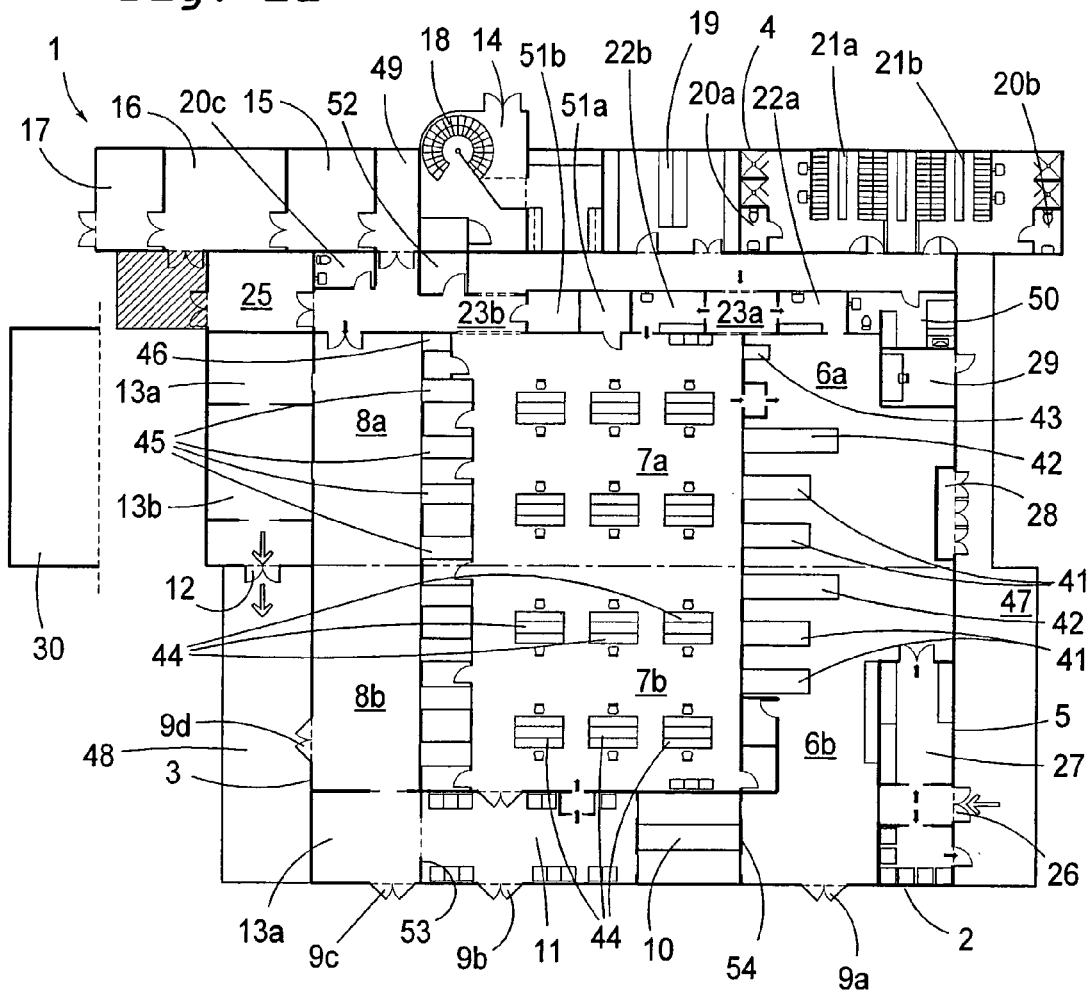
FIG. 2a shows, in a top view, in section and in principle, a lower floor in an alternative form of the original building included in the sterilization plant according to the invention.

In FIG. 2a, it is seen how a lower floor in an alternative form of the original building 1, included in the sterilization plant according to the invention, appears. No principal differences between the alternative form and the one already described are present. However, some rooms according to FIG. 2a occupies another part of the area of the building plan than the same rooms according to FIG. 1a, refer to the figures, where rooms for the same purpose have the same reference designations. Some rooms have also been added in the alternative form according to FIG. 2a, namely room 49 for general storage of waste, room 50 for first aid, material transfer rooms 51a, 51b, and broom cupboard 52. The workroom 19 for sterile-service engineer previously present has been supplemented with space for testing and data equipment. The storage space 13 for sterilized goods previously present has been divided into a space 13a having cooling facility and a space 13b that lacks this facility. An additional storage space 13a having cooling facility has been created in the storage space 11 for transport trolleys or the like by the addition of a wall 53. An additional wall 54 has been added between the contaminated zone 6b and the space 10 for the washing of transport trolleys or the like. The wall 53 is provided with one door and the wall 54 is provided with two doors. Doors are also present between the space 10 for the washing of transport trolleys or the like and the storage space 11 for transport trolleys or the like.

Figure 2B:
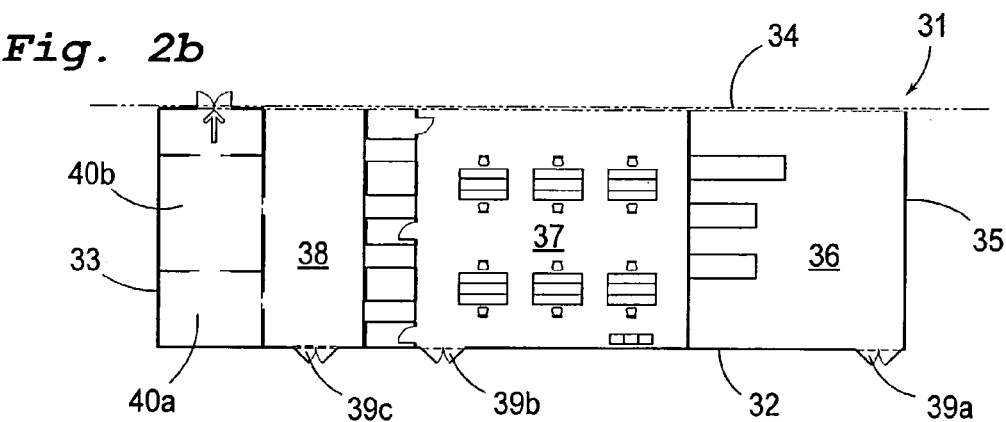
FIG. 2b shows, in a top view, in section and in principle, an alternative form of the extension module according to the invention and included in the sterilization plant according to the invention.

In FIG. 2b, it is seen how an alternative form of the extension module 31 according to the invention, and in turn included in the sterilization plant according to the invention, appears. No principal differences between the alternative form and the one already described are present. However, the storage space 40 for sterilized goods has been divided into a space 40a having cooling facility and a space 40b that lacks this facility.

Figure 3:
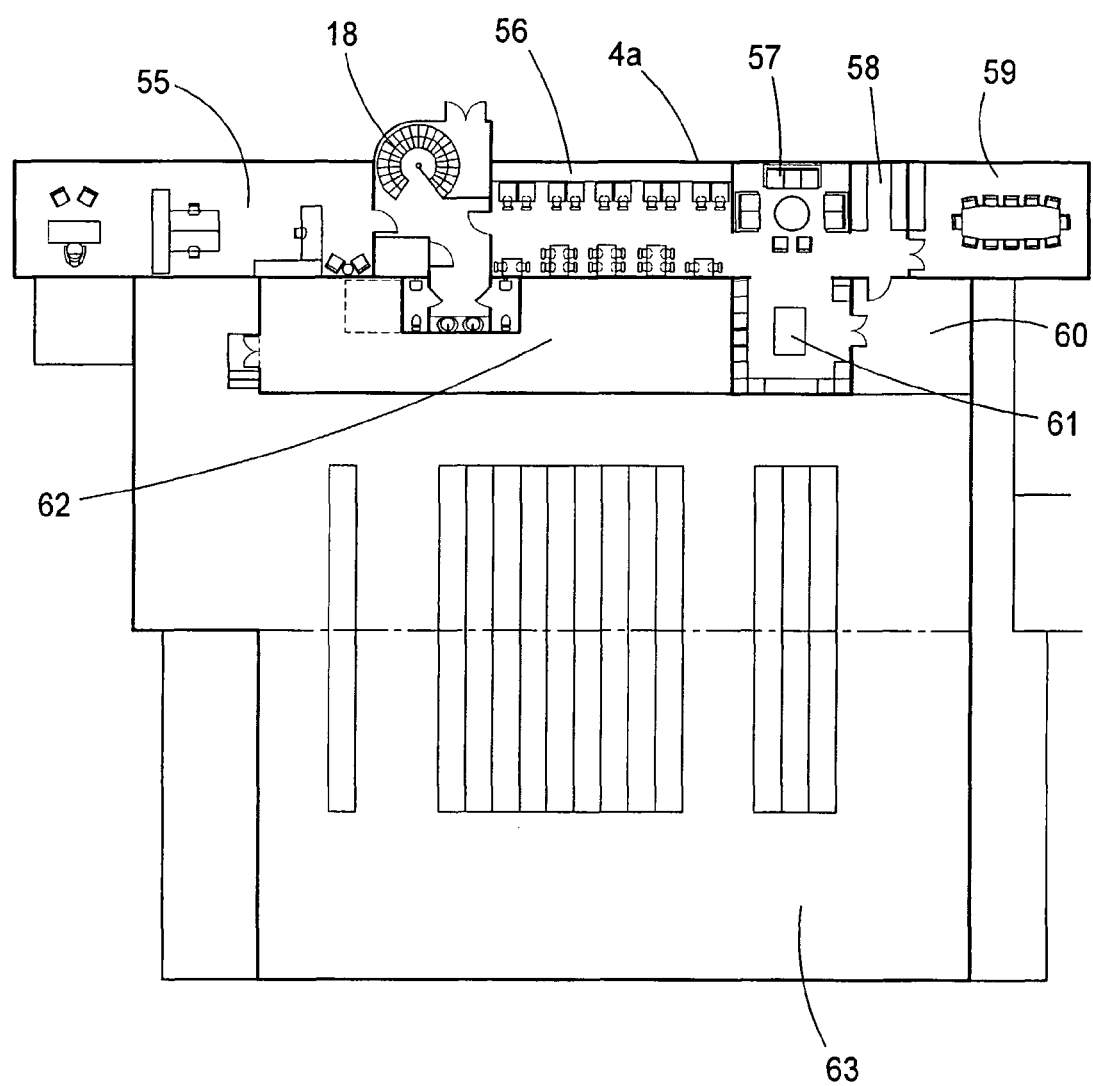
FIG. 3 shows, in a top view, partly in section and in principle, an upper floor in the original building included in the sterilization plant according to the invention.

In FIG. 3, it is seen how an upper floor in the original building, included in the sterilization plant according to the invention, appears. Inside and along the external wall 4a, a number of service spaces are present, such as office 55, canteen 56, assembly room 57, library 58, conference room 59, terrace 60, kitchen 61, and space 62 for heating, ventilating and air-conditioning equipment. The remaining area in the building plan consists of at least one roof 63 of any known expedient type.

Even if it is primarily meant to combine the original building according to FIG. 1a with the extension module, one or more, according to FIG. 1b and/or the original building according to FIG. 2a with the extension module, one or more, according to FIG. 2b, it is naturally fully possible instead to combine the original building according to FIG. 1a with the extension module, one or more, according to FIG. 2b and/or the original building according to FIG. 2a with the extension module, one or more, according to FIG. 1b. If use is made of a plurality of extension modules for an original building, the extension modules may be of the same type or of different types. Each one of all these feasible combinations is then in turn combined with the upper floor according to FIG. 3 as well as one or more roofs, of any known expedient type, on existing extension module and/or -modules in the case that this and/or these are built on-site. The upper floor may also be entirely spared if required equipment for the operation, i.e., above all heating, ventilating and air-conditioning equipment, is accommodated in existing spaces in the lower floor at the same time as the at least one roof 63 as is enlarged so that it covers the entire area of the lower floor. A sterilization plant in more planes than two is also conceivable without deviating from the general idea of the invention.

Each one of said contaminated zones 6a, 6b, 36, in said original building 1 as well as in said extension module 31, may, instead of two instrument dishwashers 41 and one multi-chamber dishwasher 42, comprise one instrument dishwasher 41 and two multi-chamber dishwashers 42. Many variations of analogous type are feasible without deviating from the general idea of the invention. In each one of said contaminated zones 6a, 6b, 36, negative pressure may prevail by the action of a ventilating system. Instead, each one of said autoclaves 45, 46 may consist of a sterilizer 45, 46 of any other known expedient type.

The invention is not limited to the embodiments shown here but may be varied within the scope of the subsequent claims.

The invention claimed is:

1. Sterilization plant for the sterilization of surgical instruments, the plant comprising at least one original building (1) having at least one first process line each extending in a linear progression, each in turn comprising at least one first contaminated zone (6a, 6b), with at least one dishwasher (41,42) washing contaminated surgical instruments, at least one first clean zone (7a, 7b) located sequentially adjacent to the at least one first contaminated zone (6a, 6b) within the linear progression, with at least one packing table (44) with clean, but not sterile, surgical instruments being packed upon the at least one packing table (44) and at least one autoclave (45), linearly located subsequent to the at least one packing table (44), with surgical instruments being sterilized within the at least one autoclave (45), and at least one first sterile zone (8a, 8b) located sequentially adjacent to the at least one first clean zone (7a, 7b) with sterile surgical instruments from the at least one autoclave being moved into the at least one sterile zone (8a, 8b) via a connection between the at least first clean zone (7a, 7b) and the at least one sterile zone (8a, 8b) within the linear progression, characterized in that said linear progression of at least one first process line, extends essentially parallel to a first one (2) of the essentially limiting external walls (2, 3, 4, 5) of said original building (1), the sterilization plant further comprising at least one extension module (31) located external to the original building (1) and next to, in a laterally off-set direction with respect to the direction of the linear progression, and essentially parallel to said first external wall (2) and comprising at least one second process line extending in a linear progression, in turn comprising at least one second contaminated zone (36), with at least one dishwasher (41,42) washing contaminated surgical instruments, at least one second clean zone (37) located sequentially adjacent to the at least one second contaminated zone (36) within the linear progression, with at least one packing table with clean, but not sterile, surgical instruments being packed upon the at least one packing table and at least one autoclave, linearly located subsequent to the at least one packing table, with surgical instruments being sterilized within the at least one autoclave, and at least one second sterile zone (38) located sequentially adjacent to the at least one second clean zone (37) with sterile surgical instruments from the at least one autoclave being moved into the at least second sterile zone (38) via a connection between the at least second clean zone (37) and the at least one sterile zone (38) within the linear progression.

2. Sterilization plant according to claim 1, wherein said first external wall (2) has at least one through passage (9a) that connects said at least one first contaminated zone (6a, 6b) and said at least one second contaminated zone (36).

3. Sterilization plant according to claim 1, wherein said first external wall (2) has at least one through passage (9b) that connects said at least one first clean zone (7a, 7b) and said at least one second clean zone (37).

4. Sterilization plant according to claim 1, wherein said first external wall (2) has at least one through passage (9c) that connects said at least one first sterile zone (8a, 8c) and said at least one second sterile zone (38).

5. Sterilization plant according to claim 1, wherein said first external wall (2) has at least one through first passage (9a) that connects said at least one first contaminated zone (6a, 6b) and said at least one second contaminated zone (36), at least one through second passage (9b) that connects said at least one first clean zone (7a, 7b) and said at least one second clean zone (37) and at least one through third passage (9c) that connects said at least one first sterile zone (8a, 8c) and said at least one second sterile zone (38), at least one of said at least one first, second and third passages (9a-c) consists of at least one emergency exit (9a-c) existing in the original building.

6. Sterilization plant according to claim 1, wherein said first external wall (2) has three emergency exits (9a-c).

7. Sterilization plant according to claim 1, comprising at least one storage space (11) intended for transport trolleys or the like, which storage space (11) is situated in said original building (1) and extends next to and essentially parallel to said first external wall (2).

8. Sterilization plant according to claim 7, at least one passage (9c) at said storage space (11) for transport trolleys.

9. Sterilization plant according to claim 1, where in said extension module (31) has an essentially rectangular shape having three extension external walls (32, 33, 35), no extension external wall being present along said first external wall (2).

10. Sterilization plant according to claim 9, wherein a first one (32) of said extension external walls (32, 33, 35) has three emergency exits (39a-c), said first extension external wall (32) being essentially opposite said first external wall (2).

11. Sterilization plant according to claim 1, wherein at least one first process line comprises at least one entrance (26), through an external wall (5) at a beginning of the linear progression, for the intake of contaminated instruments in said original building (1), at least one department (27) for manual rough washing, as well as at least one exit (48), through an external wall (3) at an end of the linear progression, for the take out of sterile instruments in said at least one first sterile zone (8a, 8b).

12. Sterilization plant according to claim 1, wherein according to claim 1, wherein the extension module (31) has an essentially rectangular shape having three extension external walls (32, 33, 35).

13. Sterilization plant according to claim 1, wherein a first one (32) of said extension external walls (32, 33, 35) has three emergency exits (39a-c).

* * * * *

UNITED STATES PATENT AND TRADEMARK OFFICE
CERTIFICATE OF CORRECTION

PATENT NO.        : 8,069,618 B2                              Page 1 of 1
APPLICATION NO.   : 11/815393
DATED             : December 6, 2011
INVENTOR(S)       : Hol Michael Larsson It is certified that error appears in the above-identified patent and that said Letters Patent is hereby corrected as shown below:

Column 3, line 61, delete the "," and insert therefore a -- . --;

Column 8, line 40, after the "," insert -- wherein according to claim 12, --.

Signed and Sealed this
Fifteenth Day of May, 2012

David J. Kappos
*Director of the United States Patent and Trademark Office*